(12) United States Patent
Nappa et al.

(10) Patent No.: US 6,369,284 B1
(45) Date of Patent: *Apr. 9, 2002

(54) CATALYTIC MANUFACTURE OF PENTAFLUOROPROPENES

(75) Inventors: Mario Joseph Nappa, Newark; V.N.Mallikarjuna Rao, Wilmington, both of DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/355,235

(22) PCT Filed: Jan. 7, 1998

(86) PCT No.: PCT/US98/00429

§ 371 Date: Jul. 26, 1999

§ 102(e) Date: Jul. 26, 1999

(87) PCT Pub. No.: WO98/33755

PCT Pub. Date: Aug. 6, 1998

Related U.S. Application Data

(60) Provisional application No. 60/036,327, filed on Jan. 31, 1997.

(51) Int. Cl.$^7$ .............................................. C07C 17/25
(52) U.S. Cl. ...................... 570/156; 570/157; 570/158
(58) Field of Search ................................ 570/156, 158, 570/157

(56) References Cited

U.S. PATENT DOCUMENTS

| | | |
|---|---|---|
| 2,478,933 A | 8/1949 | Bratton et al. |
| 2,599,631 A | 6/1952 | Harmon |
| 3,607,955 A | 9/1971 | Gardner |
| 4,978,649 A | 12/1990 | Surovikin et al. |
| 5,136,113 A | 8/1992 | Rao |
| 5,396,000 A | 3/1995 | Nappa et al. |
| 5,559,069 A | 9/1996 | Rao et al. |
| 5,945,573 A * | 8/1999 | Nappa et al. ................ 570/157 |
| 6,093,859 A * | 7/2000 | Nappa et al. ................ 570/157 |

FOREIGN PATENT DOCUMENTS

| | | |
|---|---|---|
| EP | 0 461 297 A1 | 12/1991 |
| EP | 0644173 A1 * | 12/1993 |
| EP | 0 644 173 A1 | 3/1995 |
| EP | 0 726 243 A1 | 8/1996 |
| FR | 1 330 146 A | 5/1963 |
| JP | 9-67281 | 3/1997 |
| WO | WO 98/22414 | 5/1998 |

OTHER PUBLICATIONS

Patent Abstracts of Japan, JP 63 048235A, Feb. 29, 1988.
Abstract No. 126:27717w, CA Selects: Organofluorine Chemistry, Issue No. 11, p. 5, 1997.

* cited by examiner

Primary Examiner—Alan Siegel

(57) ABSTRACT

A process is disclosed for the manufacture of a pentafluoropropene of the formula: $CFX=CYCF_3$ where X is selected from H and F and where Y is F when X is H and Y is H when X is F. The process involves contacting a hexafluoropropane of the formula: $CF_2XCHYCF_3$ at a temperature of from about 200° C. to 500° C. with a catalyst, optionally in the presence of an inert gas. Suitable catalysts include (1) catalysts of (a) at least one compound selected from the oxides, fluorides and oxyfluorides of magnesium, zinc and mixtures of magnesium and zinc, and optionally (b) at least one compound selected from the oxides, fluorides and oxyfluorides of aluminum; provided that the atomic ratio of aluminum to the total of magnesium and zinc in said catalyst is about 1:4, or less (e.g., 1:9), (2) lanthanum fluoride, (3) fluorided lanthanum oxide, (4) activated carbon, and (5) three-dimensional matrix carbonaceous materials.

19 Claims, No Drawings

CATALYTIC MANUFACTURE OF PENTAFLUOROPROPENES

This application represents a national filing under 35 U.S.C. 371 of International Application No. PCT/US98/00429 filed Jan. 7, 1998 and claims priority of U.S. Provisional Application No. 60/036,327 filed Jan. 31, 1997.

FIELD OF THE INVENTION

This invention relates to processes for the production of pentafluoropropenes, and more particularly, to a catalytic process for the dehydrofluorination of hexafluoropropanes to pentafluoropropenes.

BACKGROUND

Hydrofluoropropenes are useful as materials for the preparation of fluoroplastics, fluoroelastomers and as monomers in the preparation of fluoropolymers.

European Patent Application EP 726 243 discloses a process for the manufacture of 1,2,3,3,3-pentafluoropropene (HFC-1225ye) by the dehydrofluorination of 1,1,1,2,3,3-hexafluoropropane (HFC-236ea). The dehydrofluorination is done in the vapor phase in the presence of a trivalent chromium oxide or partly fluorinated trivalent chromium oxide catalyst.

U.S. Pat. No. 5,396,000 discloses that HFC-236ea can be dehydrofluorinated to HFC-1225ye in the vapor phase in the presence of a catalyst selected from the group consisting of aluminum fluoride, fluorided alumina, metal supported on aluminum fluoride, metal supported on fluorided alumina, and mixtures thereof.

SUMMARY OF THE INVENTION

A process is provided for the manufacture of a pentafluoropropene of the formula $CFX=CYCF_3$ where X is selected from H and F and where Y is F when X is H and Y is H when X is F. The process comprises contacting a hexafluoropropane of the formula $CF_2XCHYCF_3$ at a temperature of from about 200° C. to 500° C. with a catalyst, optionally in the presence of an inert gas. The catalyst is selected form the group consisting of (1) catalysts of (a) at least one compound selected from the oxides, fluorides and oxyfluorides of magnesium, zinc and mixtures of magnesium and zinc, and optionally (b) at least one compound selected from the oxides, fluorides and oxyfluorides of aluminum, provided that the atomic ratio of aluminum to the total of magnesium and zinc in said catalyst is about 1:4, or less (e.g., 1:9), (2) lanthanum fluoride, (3) fluorided lanthanum oxide, (4) activated carbon, and (5) three-dimensional matrix carbonaceous materials.

DETAILED DISCUSSION

This invention provides a process for producing cis- and trans-1,2,3,3,3-pentafluoropropene (i.e., $CF_3CF=CHF$ or 1225ye) from 1,1,1,2,3,3-hexafluoropropane (i.e., $CF_3CHFCHF_2$, or HFC-236ea). A process is also provided for producing 1,1,3,3,3-pentafluoropropene (i.e., $CF_3CH=CF_2$ or 1225zc) from 1,1,1,3,3,3-hexafluoropropane (i.e., $CF_3CH_2CF_3$, or HFC-236fa). HFC-236ea and HFC-236fa can be prepared by known art methods. For example, $CF_3CH_2CF_3$ can be prepared by contacting a mixture of hydrogen fluoride and 1,1,1,3,3,3-hexachloropropane (i.e., $CCl_3CH_2CCl_3$) in the vapor phase in the presence of a trivalent chromium catalyst as disclosed in U.S. Pat. No. 5,414,165 and $CF_3CHFCHF_2$ can be prepared by hydrogenation of hexafluoropropene (i.e., $CF_3CF=CF_2$) in the the presence of a Pd/C catalyst.

In accordance with this invention, $CF_3CHFCHF_2$ is dehydrofluorinated to $CF_3CF=CHF$ and $CF_3CH_2CF_3$ is dehydrofluorinated to $CF_3CH=CF_2$ over a selected catalyst.

Suitable fluorided lanthanum oxide compositions can be prepared in any manner analogous to those known to the art for the preparation of fluorided alumina. For example, the catalyst composition can be prepared by fluorination of lanthanum oxide.

Suitable catalyst compositions can also be prepared by precipitation of lanthanum as the hydroxide which is thereafter dried and calcined to form an oxide, a technique well known to the art. The resulting oxide can then be pretreated as described herein.

The catalyst composition can be fluorinated to the desired fluorine content by treating with a fluorine-containing compound at elevated temperatures, e.g., at about 200° C. to about 450° C. The pretreatment with a vaporizable fluorine-containing compound such as HF, $SF_4$, $CCl_3F$, $CCl_2F_2$, $CHF_3$, $CHClF_2$ or $CCl_2FCClF_2$ can be done in any convenient manner including in the reactor which is to be used for carrying out the dehydrofluorination reaction. By vaporizable fluorine-containing compound is meant a fluorine-containing compound which, when passed over the catalyst at the indicated conditions, will fluorinate the catalyst to the desired degree.

A suitable catalyst may be prepared, for example, as follows:

$La_2O_3$ is dried until essentially all moisture is removed, e.g., for about 18 hours at about 400° C. The dried catalyst is then transferred to the reactor to be used. The temperature is then gradually increased to about 400° C. while maintaining a flow of $N_2$ through the reactor to remove any remaining traces of moisture from the catalyst and the reactor. The temperature is then lowered to about 200° C. and the vaporizable fluorine-containing compound is passed through the reactor. If necessary, nitrogen or other inert gases can be used as diluents. The $N_2$ or other inert diluents can be gradually reduced until only the vaporizable fluorine-containing compound is being passed through the reactor. At this point the temperature can be increased to about 450° C. and held at that temperature to convert the $La_2O_3$ to a fluorine content corresponding to at least 80% $LaF_3$ by weight, e.g., for 15 to 300 minutes, depending on the flow of the fluorine containing compound and the catalyst volume.

Another suitable procedure for the catalyst preparation is to add ammonium hydroxide to a solution of $La(NO_3)_3 \cdot 6H_2O$. The ammonium hydroxide is added to the nitrate solution to a pH of about 9.0 to 9.5. At the end of the addition, the solution is filtered, the solid obtained is washed with water, and slowly heated to about 400° C., where it is calcined. The calcined product is then treated with a suitable vaporizable fluorine-containing compound as described above.

Carbon from any of the following sources are useful for the process of this invention; wood, peat, coal, coconut shells, bones, lignite, petroleum-based residues and sugar. Commercially available carbons which may be used in this invention include those sold under the following trademarks: Barneby & Sutcliffe™, Darco™, Nucharm, Columbia JXN™, Columbia LCK™, Calgon PCB, Calgon BPL™, Westvaco™, Norit™ and Barnaby Cheny NB™. The carbon support can be in the form of powder, granules, or pellets, or the like.

Carbons include acid-washed carbons (e.g., carbons which have been treated with hydrochloric acid or hydrochloric acid followed by hydrofluoric acid). Acid treatment is typically sufficient to provide carbons which contain less than 1000 ppm of ash. Suitable acid treatment of carbons is described in U.S. Pat. No. 5,136,113. The carbons of this invention also include three dimensional matrix porous carbonaceous materials. Examples are those described in U.S. Pat. No. 4,978,649, which is hereby incorporated by reference herein in its entirety. Of note are three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

Other preferred catalysts include catalysts consisting essentially of magnesium fluoride, and catalysts consisting essentially of magnesium fluoride and at least one compound selected from the oxides, fluorides and oxyfluorides of aluminum.

A suitable catalyst may be prepared, for example, as follows:

Magnesium oxide is dried until essentially all water is removed, e.g., for about 18 hours at about 100° C. The dried material is then transferred to the reactor to be used. The temperature is then gradually increased to about 400° C. while maintaining a flow of nitrogen through the reactor to remove any remaining traces of moisture from the magnesium oxide and the reactor. The temperature is then lowered to about 200° C. and a fluoriding agent such as HF or other vaporizable fluorine containing compounds such as $SF_4$, $CCl_3F$, $CCl_2F_2$, $CHF_3$ or $CCl_2FCClF_2$, optionally diluted with an inert gas such as nitrogen is passed through the reactor. The inert gas or nitrogen can be gradually reduced until only HF or other vaporizable fluorine containing compounds is being passed through the reactor. At this point the temperature can be increased to about 450° C. and held at that temperature to convert the magnesium oxide to a fluoride content corresponding to at least 40% by weight, e.g., for 15 to 300 minutes, depending on the fluoriding agent flowrate and the catalyst volume. The fluorides are in the form of magnesium fluoride or magnesium oxyfluoride; the remainder of the catalyst is magnesium oxide. It is understood in the art that fluoriding conditions such as time and temperature can be adjusted to provide higher than 40 weight% fluoride-containing material.

Another suitable procedure for the catalyst preparation is to add ammonium hydroxide to a solution of magnesium nitrate and if present zinc nitrate and/or aluminum nitrate. The ammonium hydroxide is added to the nitrate solution to a pH of about 9.0 to 9.5. At the end of the addition, the solution is 20 filtered, the solid obtained is washed with water, dried and slowly heated to 500° C., where it is calcined. The calcined product is then treated with a suitable fluorine-containing compound as described above.

Yet another procedure for the preparation of metal (i.e., magnesium optionally containing also zinc and/or aluminum) fluoride catalysts containing one or more metal fluorides is to treat an aqueous solution of the metal(s) halide(s) or nitrate(s) in deionized water was treated with 48% aqueous HF with stirring. Stirring is continued overnight and the slurry evaporated to dryness on a steam bath. The dried solid is then calcined in air at 400° C. for about four hours, cooled to room temperature, crushed and sieved to provide material for use in catalyst evaluations.

The physical shape of the catalyst is not critical and may, for example, include pellets, powders or granules.

The catalytic dehydrofluorination of $CF_3CH_2CF_3$ and $CF_3CHFCHF_2$ is suitably conducted at a temperature in the range of from about 200° C. to about 500° C. and preferably from about 375° C. to about 450° C. The contact time is typically from about 1 to about 450 seconds, preferably from about 10 to about 120 seconds.

The reaction pressure can be subatmospheric, atmospheric or superatmospheric. Generally, near atmospheric pressures are preferred. However, the dehydrofluorination of $CF_3CH_2CF_3$ can be beneficially run under reduced pressure (i.e., pressures less than one atmosphere).

The reaction can be done in the presence of inert gases such as nitrogen and argon. It has been found that inert gases can be used to increase the dehydrofluorination (DHF) of $CF_3CH_2CF_3$ to $CF_3CH=CF_2$. Of note are processes where the mole ratio of inert gas to $CF_3CH_2CF_3$ fed to the dehydrofluorination is from about 5:1 to 1:1. Nitrogen is a preferred inert gas. Inert gases have essentially no effect on the DHF of $CF_3CHFCHF_2$ to $CF_3CF=CHF$.

Unreacted starting material can be recycled to the reactor for the production of additional $CF_3CF=CHF$ (1225ye) and $CF_3CH=CF_2$ (1225zc). The hydrofluoropropenes 1225ye and 1225zc may be recovered from the reaction product and any unreacted hydrofluoropropanes by conventional procedures such as distillation.

The process of this invention can be carried out readily in the vapor phase using well known chemical engineering practice.

Without further elaboration, it is believed that one skilled in the art can, using the description herein, utilize the present invention to its fullest extent. The following specific embodiments are to be construed as illustrative, and not as constraining the remainder of the disclosure in any way whatsoever.

EXAMPLES

| Legend | |
|---|---|
| 236fa is $CF_3CH_2CF_3$ | 1225zc is $CF_3CH=CF_2$ |
| 236ea is $CF_3CHFCHF_2$ | 1225ye is cis- and trans-$CF_3CF=CHF$ |

CT is contact time

PREPARATION OF CATALYSTS

General Procedure for the Preparation of Magnesium Fluoride Containing Catalysts Unless stated otherwise, the following general procedure was followed for the preparation of magnesium fluoride catalysts containing one or more metal fluorides. An aqueous solution of the metal(s) halide(s) or nitrate(s) in deionized water was treated with 48% aqueous HF with stirring. Stirring was continued overnight and the slurry evaporated to dryness on a steam bath. The dried solid was then calcined in air at 400° C. for about four hours, cooled to room temperature, crushed and sieved to provide a 12–20 mesh (1.68–0.84 mm) fraction which was used in catalyst evaluations.

Catalyst A—Fluorided Lanthanum Oxide

La(NO$_3$)$_3$.6H$_2$O (98.4 g) was dissolved in deionized water (1.5 L) in a 2 L beaker provided with an agitator. A solution (200 mL) of NH$_4$OH and deionized water (1/1, volume/volume) was added during a period of 10 minutes to the agitated solution. The pH of the solution was 9.5 after this addition. The slurry was filtered and dried in air at 125° C. for about 18 hours, followed by calcination at 350° C. in air for an additional 8 hours. The product (46.8 g) was compressed into wafers and screened. Particles in the 12×20 mesh (1.4 mm×0.83 mm) range were used for the examples. The granulated catalyst precursor (15 mL, 17.6 g) was placed in a ⅝" (1.58 cm) Inconel® nickel alloy reactor heated in a fluidized sand bath. It was heated to 175° C. in a flow of nitrogen (50 cc/min) at which time HF flow (50 cc/min) was also started through the reactor. As the initial exotherm monitored by an internal thermocouple subsided (2–3 hours), nitrogen flow was decreased to 20 cc/min and HF flow increased to 80 cc/min. The reactor temperature was gradually increased to 400° C. during a 3–4 hour period and maintained at 400° C. for an additional 30 minutes. At the end of this period the reactor was brought to the desired operating temperature for catalyst evaluation.

Catalyst B—MgF$_2$

Following the general procedure described above for the preparation of fluorinated catalysts, a MgF$_2$ catalyst was prepared from 150.0 g of Mg(NO$_3$)$_2$.6H$_2$O, 500 mL deionized water and 75 mL 48% aqueous HF.

Catalyst C—MgF$_2$/AlF$_3$ (43:1):

Following the general procedure described above for the preparation of fluorinated catalysts, a MgF$_2$/AlF$_3$ catalyst having a nominal magnesium to aluminum atomic ratio of 43:1 was prepared from 251.28 g Mg(NO$_3$)$_2$.6H$_2$O, 7.50 g Al(NO$_3$)$_3$.9H$_2$O and 100 mL 48% aqueous HF.

Catalyst D—MgF$_2$/AlF$_3$ (9:1):

Following the general procedure described above for the preparation of fluorinated catalysts, a MgF$_2$/AlF$_3$ catalyst having a nominal magnesium to aluminum atomic ratio of 9:1 was prepared from 237.6 g Mg(NO$_3$)$_2$.6H$_2$O, 34.76 g Al(NO$_3$)$_3$.9H$_2$O and 120 mL 48% aqueous HF.

Catalyst E–H

Commercial samples of acid-washed coconut shell carbon were used.

Catalyst I

Porous carbonaceous material prepared substantially as described in U.S. Pat. No. 4,9789,649 was used.

Catalyst J

A commercial sample of coconut shell carbon (not acid-washed) was used.

Catalyst K—Fluorided Magnesia

A commercial sample of magnesium oxide which was pelletized and ground to 12/20 mesh (1.68/0.84 mm) was heated to 200° C. for two hours while purging with nitrogen (50 sccm, 8.3×10$^{-7}$ m$^3$/s). The nitrogen was continued at 50 sccm (8.3×10$^{-7}$ m$^3$/s), and the catalyst contacted with HF (50 sccm, 8.3×10$^{-7}$ m$^3$/s) for 15 minutes. The HF flow was raised to 80 sccm (1.3×10$^{-6}$ m$^3$/s) and the nitrogen flow reduced to 20 sccm (3.3×10$^{-7}$ m$^3$/s) for 25 minutes. The temperature was raised to 250° C. for 75 minutes, 300° C. for 75 minutes, 350° C. for 75 minutes, and 400° C. for 75 minutes while maintaining the flows of HF and nitrogen to provide a fluorided magnesia catalyst.

Catalyst L—Fluorided Alumina

A commercial sample of gamma-alumina extrudate (10.6 g, 15 mL, 1/12", 2.1 mm) was dried at 110° C. in air for 18 hours in a ⅝" (1.58 cm) Inconel® nickel alloy reactor heated in a fluidized sand bath. The temperature was raised to 200° C. and HF and nitrogen (1:4 molar ratio) were passed through the alumina. The nitrogen flow was decreased with time until neat HF was being passed through the reactor. At this point the temperature was gradually raised to 450° C. and maintained there for 30 minutes. The fluorine content of the fluorided alumina corresponded to an AlF$_3$ content of at least 50%.

Catalyst M—Chromium Oxide

A commercial sample (39.9 g, 30 mL) of chromium oxide (Cr$_2$O$_3$) was used.

Table 1 lists the catalyst, its weight and volume and the examples for which the listed catalyst was used.

Examples 1–9

$$CF_3CHFCHF_2 \rightarrow CF_3CF=CHF+HF$$

A 15 in. (38.1 cm)×⅜ in (0.95 cm) Hastelloy™ nickel alloy tube was filled with the amounts of catalyst shown in Table 1. The reactor was heated to the temperatures recorded in Table 2. The flow of 1,1,1,2,3,3-hexafluoropropane was begun to the reactor with the contact times shown. The dehydrofluorination results (mole %) are shown in Table 2.

TABLE 1

| Ex. | Cat. | Wt. (g) | Vol. (mL) |
|---|---|---|---|
| 1, 10 | A | 17.6 | 15 |
| 2 | B | 8.9 | 10 |
| 3, 11 | C | 8.4 | 10 |
| 4, 12 | D | 8.0 | 10 |
| 5 | E | 8.3 | 20 |
| 6 | F | 7.4 | 20 |
| 7 | G | 7.3 | 20 |
| 8 | H | 8.7 | 20 |
| 9 | I | 10 | 20 |
| 13 | H | 4.7 | 10 |
| 14 | I | 5.3 | 10 |
| 15 | J | 6.2 | 10 |
| 16 | K | 10.4 | 13 |
| A, B | L | 10.6 | 15 |
| C | M | 39.9 | 30 |

TABLE 2

| Ex. | Cat. | T (° C.) | CT | % 236ea | % 1225ye |
|---|---|---|---|---|---|
| 1 | A | 350 | 60 | 99.5 | 0.3 |
|   |   | 400 | 60 | 98.0 | 1.9 |
|   |   | 450 | 60 | 92.9 | 7.0 |
|   |   | 500 | 60 | 83.7 | 16.1 |
| 2 | B | 350 | 120 | 99.9 | 0.1 |
|   |   | 400 | 120 | 99.4 | 0.5 |
|   |   | 450 | 120 | 97.8 | 2.2 |
| 3 | C | 350 | 120 | 96.3 | 3.6 |
|   |   | 400 | 120 | 89.7 | 10.3 |
|   |   | 425 | 120 | 83.8 | 16.2 |
|   |   | 450 | 120 | 75.5 | 24.5 |
|   |   | 450 | 60 | 85.2 | 14.7 |
| 4 | D | 350 | 120 | 83.2 | 16.8 |
|   |   | 400 | 120 | 64.4 | 35.6 |
|   |   | 450 | 120 | 42.2 | 57.8 |
| 5 | E | 350 | 120 | 99.0 | 0.9 |
|   |   | 375 | 120 | 97.1 | 2.7 |
|   |   | 400 | 120 | 88.2 | 11.7 |
|   |   | 425 | 120 | 35.8 | 63.2 |
|   |   | 450 | 120 | 7.5 | 80.1 |
| 6 | F | 350 | 120 | 98.9 | 1.0 |
|   |   | 375 | 120 | 97.2 | 2.7 |
|   |   | 400 | 120 | 86.1 | 13.3 |
|   |   | 425 | 120 | 31.6 | 64.9 |
|   |   | 450 | 120 | 9.9 | 77.8 |
| 7 | G | 350 | 120 | 99.8 | 0.1 |

TABLE 2-continued

| Ex. | Cat. | T (° C.) | CT | % 236ea | % 1225ye |
|---|---|---|---|---|---|
|  |  | 400 | 120 | 79.8 | 20.2 |
|  |  | 425 | 120 | 36.6 | 58.6 |
| 8 | H | 350 | 120 | 99.5 | 0.5 |
|  |  | 375 | 120 | 83.2 | 16.8 |
|  |  | 400 | 120 | 60.9 | 39.0 |
|  |  | 425 | 120 | 29.1 | 69.2 |
|  |  | 450 | 120 | 10.8 | 73.1 |
| 9 | I | 325 | 120 | 93.1 | 6.9 |
|  |  | 350 | 120 | 84.1 | 15.9 |
|  |  | 375 | 120 | 67.6 | 32.4 |
|  |  | 400 | 120 | 48.1 | 51.9 |

Comparative Example A

The same apparatus and procedure as used for Examples 1–9 were used for comparative example A. The results are shown in Table A.

TABLE A

| Ex. | Cat. | T (° C.) | CT | % 236ea | % 1225ye |
|---|---|---|---|---|---|
| A | L | 325 | 30 | 69.4 | 28.5 |
|  |  | 350 | 60 | 46.7 | 52.3 |
|  |  | 400 | 60 | 8.3 | 89.9 |

Examples 10–16

$CF_3CH_2CF_3 \rightarrow CF_3CF=CH_2 + HF$

The same apparatus and procedure as used for Examples 1–9 were used for Examples 10–15. The results are shown in Table 3. Examples 10–12 are reported in mole %; Examples 13–15 are reported in area %.

TABLE 3

| Ex. | Cat. | T (° C.) | CT | [A]:[B]$^a$ | % 236fa | % 1225zc |
|---|---|---|---|---|---|---|
| 10 | A | 350 | 60 |  | 98.5 | 1.3 |
|  |  | 375 | 60 |  | 96.8 | 3.1 |
|  |  | 450 | 60 |  | 84.7 | 15.2 |
|  |  | 500 | 60 |  | 56.8 | 42.7 |
| 11 | C | 350 | 120 |  | 91.3 | 8.7 |
|  |  | 400 | 120 |  | 78.1 | 21.8 |
|  |  | 450 | 120 |  | 55.1 | 44.7 |
|  |  | 450 | 60 |  | 47.1 | 52.6 |
|  |  | 450 | 30 |  | 49.3 | 50.4 |
| 12 | D | 350 | 120 |  | 91.2 | 8.7 |
|  |  | 400 | 120 |  | 78.3 | 21.6 |
|  |  | 400 | 60 |  | 71.5 | 28.4 |
|  |  | 450 | 120 |  | 54.2 | 45.6 |
|  |  | 450 | 60 |  | 45.5 | 54.2 |
| 13 | H | 350 | 60 | — | 94.1 | 5.8 |
|  |  | 350 | 120 | — | 91.8 | 8.2 |
|  |  | 350 | 120 | 1:2 | 96.3 | 3.7 |
|  |  | 350 | 120 | 1:1 | 95.7 | 4.2 |
|  |  | 375 | 60 | — | 86.5 | 13.4 |
|  |  | 375 | 120 | — | 87.9 | 11.9 |
|  |  | 375 | 120 | 1:2 | 79.9 | 20.1 |
|  |  | 375 | 120 | 1:1 | 95.7 | 4.2 |
|  |  | 400 | 60 | — | 81.9 | 17.7 |
|  |  | 400 | 120 | — | 85.0 | 14.1 |
|  |  | 400 | 120 | 1:2 | 72.7 | 26.7 |
|  |  | 400 | 120 | 1:1 | 76.7 | 22.6 |
|  |  | 425 | 40 | — | 74.4 | 25.0 |
|  |  | 425 | 120 | — | 76.2 | 21.2 |
|  |  | 425 | 120 | 1:2 | 63.2 | 35.3 |

TABLE 3-continued

| Ex. | Cat. | T (° C.) | CT | [A]:[B]$^a$ | % 236fa | % 1225zc |
|---|---|---|---|---|---|---|
|  |  | 425 | 120 | 1:1 | 67.3 | 31.2 |
| 14 | I | 350 | 60 | — | 96.1 | 3.8 |
|  |  | 350 | 120 | — | 94.6 | 5.4 |
|  |  | 350 | 120 | 1:1 | 95.4 | 4.6 |
|  |  | 375 | 60 | — | 93.2 | 6.7 |
|  |  | 375 | 120 | — | 90.3 | 9.5 |
|  |  | 375 | 120 | 1:2 | 95.7 | 4.3 |
|  |  | 375 | 120 | 1:1 | 94.4 | 5.6 |
|  |  | 400 | 60 | — | 90.2 | 9.7 |
|  |  | 400 | 40 | — | 93.8 | 6.1 |
|  |  | 400 | 120 | — | 91.3 | 8.4 |
|  |  | 400 | 120 | 1:2 | 96.2 | 3.8 |
|  |  | 400 | 120 | 1:1 | 93.7 | 6.2 |
|  |  | 425 | 40 | — | 74.6 | 25.3 |
|  |  | 425 | 120 | — | 75.2 | 24.6 |
|  |  | 425 | 120 | 1:2 | 67.1 | 32.8 |
|  |  | 425 | 120 | 1:1 | 68.9 | 31.0 |
| 15 | J | 350 | 60 | — | 93.1 | 6.7 |
|  |  | 350 | 120 | — | 91.8 | 8.0 |
|  |  | 350 | 120 | 1:2 | 93.5 | 6.5 |
|  |  | 350 | 120 | 1:1 | 91.7 | 8.2 |
|  |  | 375 | 60 | — | 86.2 | 13.6 |
|  |  | 375 | 120 | — | 86.9 | 12.8 |
|  |  | 375 | 120 | 1:2 | 80.3 | 19.6 |
|  |  | 375 | 120 | 1:1 | 81.7 | 18.2 |
|  |  | 400 | 60 | — | 80.0 | 19.7 |
|  |  | 400 | 120 | — | 79.6 | 20.1 |
|  |  | 400 | 120 | 1:2 | 71.6 | 28.1 |
|  |  | 400 | 120 | 1:1 | 75.6 | 23.6 |
|  |  | 425 | 40 | — | 73.8 | 25.7 |
|  |  | 425 | 120 | — | 75.4 | 22.3 |
|  |  | 425 | 120 | 1:2 | 63.3 | 35.4 |
|  |  | 425 | 120 | 1:1 | 67.0 | 31.7 |
| 16 | K | 421 | 60 | 1:1 | 81.4 | 16.8 |

$^a$[A]:[B] is the molar ratio of 236fa to nitrogen in the initial reactor feed. No nitrogen was used for the runs where there is no entry in this column.

Comparative Examples B and C

The same apparatus and procedure as used for Examples 1–9 were used for comparative example B and C. The results are shown in Table B.

TABLE B

| Ex. | Cat. | T (° C.) | CT | % 236fa | % 225zc |
|---|---|---|---|---|---|
| B | L | 300 | 30 | 96.9 | 0.9 |
|  |  | 350 | 30 | 90.5 | 7.1 |
| C | M | 350 | 30 | 92.7 | 7.1 |
|  |  | 350 | 60 | 89.0 | 10.8 |
|  |  | 350 | 30 | 88.4 | 11.5 |
|  |  | 350 | 15 | 87.1 | 12.7 |
|  |  | 400 | 15 | 74.5 | 24.8 |
|  |  | 400 | 15 | 83.3 | 16.2 |
|  |  | 400 | 10 | 87.9 | 11.9 |

What is claimed is:
1. Process for the manufacture of a pentafluoropropene of the formula $CFX=CYCF_3$ where X is selected from H and F and where Y is F when X is H and Y is H when X is F, comprising:
   contacting a hexafluoropropane of the formula $CF_2XCHYCF_3$ at a temperature of from about 200° C. to 500° C. with a catalyst, optionally in the presence of and inert gas; said catalyst being selected form the group consisting of (1) catalysts of (a) at least one compound selected from the oxides, fluorides and oxyfluorides of magnesium, zinc and mixtures of magnesium and zinc, and optionally (b) at least one compound selected from the oxides, fluorides and oxyfluo- rides of aluminum; provided that the atomic ratio of aluminum to the total of magnesium and zinc in said catalyst is about 1:4, or less, (2) lanthanum fluoride, (3) fluorided lanthanum oxide, and (4) three-dimensional matrix carbonaceous materials obtained by introducing gaseous or vaporous carbon-containing compounds into a mass of granules of carbonaceous materials, decomposing the carbon-containing compounds to deposit carbon on the surface of the granules, and treating the resulting material with an activator gas comprising steam.

2. The process of claim 1 wherein $CF_3CH_2CF_3$ is dehydrofluorinated to provide $CF_3CH=CF_2$.

3. The process of claim 2 wherein an inert gas is fed to the dehydrofluorination in a mole ratio to $CF_3CH_2CF_3$ of from about 5:1 to 1:1.

4. The process of claim 3 wherein the inert gas is nitrogen.

5. The process of claim 2 wherein the dehydrofluorination is run under reduced pressure.

6. A process for the manufacture of a pentafluoropropene of the formula $CFX=CYCF_3$ where X is selected from H and F and where Y is F when X is H and Y is H when X is F, comprising:
  contacting a hexafluoropropane of the formula $CF_2XCHYCF_3$ at a temperature of from about 200° C. to 500° C. with a catalyst of (a) at least one compound selected from the oxides, fluorides and oxyfluorides of magnesium, zinc and mixtures of magnesium and zinc, and optionally (b) at least one compound selected from the oxides, fluorides and oxyfluorides of aluminum; provided that the atomic ratio of aluminum to the total of magnesium and zinc in said catalyst is about 1:4, or less.

7. The process of claim 6 wherein the catalyst consists essentially of magnesium fluoride.

8. The process of claim 7 where $CF_3CH_2CF_3$ is dehydrofluorinated to provide $CF_3CH=CF_2$.

9. The process of claim 6 wherein the catalyst consists essentially of magnesium fluoride and at least one compound selected from the oxides, fluorides and oxyfluorides of aluminum.

10. The process of claim 9 where $CF_3CH_2CF_3$ is dehydrofluorinated to provide $CF_3CH=CF_2$.

11. The process of claim 6 where $CF_3CH_2CF_3$ is dehydrofluorinated to provide $CF_3CH=CF_2$.

12. The process of claim 11 wherein an inert gas is fed to the dehydrofluorination in a mole ratio to $CF_3CH_2CF_3$ of from about 5:1 to 1:1.

13. The process of claim 12 wherein the inert gas is nitrogen.

14. The process of claim 11 wherein the dehydrofluorination is run under reduced pressure.

15. A process for the manufacture of a pentafluoropropene of the formula $CFX=CYCF_3$ where X is selected from H and F and where Y is F when X is H and Y is H when X is F, comprising:
  contacting a hexafluoropropane of the formula $CF_2XCHYCF_3$ at a temperature of from about 200° C. to 500° C. with a lanthanum fluoride catalyst or a fluorided lanthanum oxide catalyst.

16. The process of claim 15 where $CF_3CH_2CF_3$ is dehydrofluorinated to provide $CF_3CH=CF_2$.

17. The process of claim 16 wherein an inert gas is fed to the dehydrofluorination in a mole ratio to $CF_3CH_2CF_3$ of from about 5:1 to 1:1.

18. The process of claim 17 wherein the inert gas is nitrogen.

19. The process of claim 16 wherein the dehydrofluorination is run under reduced pressure.

* * * * *